United States Patent
Brodkin et al.

[11] Patent Number: 6,090,194
[45] Date of Patent: Jul. 18, 2000

[54] CUBIC LEUCITE-CONTAINING DENTAL PORCELAINS

[75] Inventors: Dmitri Brodkin, West Orange; Carlino Panzera, BelleMead, both of N.J.

[73] Assignee: Jeneric/Pentron Incorporated, Wallingford, Conn.

[21] Appl. No.: 09/168,803

[22] Filed: Oct. 8, 1998

Related U.S. Application Data
[60] Provisional application No. 60/062,345, Oct. 15, 1997.

[51] Int. Cl.$^7$ .................. C03C 10/10; A61C 13/683; A61C 13/00
[52] U.S. Cl. .................. 106/35; 433/202.1; 433/201.1; 301/6; 301/32; 301/66; 301/64; 301/70; 301/72
[58] Field of Search .................. 106/35; 501/6, 501/32, 59, 66, 64, 70, 72; 433/202.1, 201.1

[56] References Cited

U.S. PATENT DOCUMENTS

| | | | |
|---|---|---|---|
| 3,236,662 | 2/1966 | MacDowell | 106/39 |
| 3,723,140 | 3/1973 | Beall et al. | 106/39.6 |
| 3,726,695 | 4/1973 | Beall et al. | 106/39 |
| 4,604,366 | 8/1986 | Kacicz et al. | 501/6 |
| 4,798,536 | 1/1989 | Katz | 433/212.1 |
| 5,192,722 | 3/1993 | Bedard et al. | 501/128 |
| 5,204,077 | 4/1993 | Mori et al. | 423/328.2 |
| 5,994,246 | 11/1999 | Denry | 501/32 |

FOREIGN PATENT DOCUMENTS 0 543 065  5/1993  European Pat. Off. .

OTHER PUBLICATIONS

Hahn et al, "Importance of the glass Ceramic Syatem K20–Al203–SiO2 in Dental Porcelain", Ceramic Formum Int./Ber. Dt. Keram. Ges. vol. 57, No. 9–10, pp. 208–214, 1980 no month.

Denry IL, Holloway JA, Rosenstiel SF; Crystallization Kinetics of a Low–Expansion Feldspar Glass for Dental Applications; Journal of Biomedical Materials Research, (Sep. 5, 1998) 41 (3) 398–404.

Denry IL, Holloway JA, Rosenstiel SF;Effect of Ion–Exchange on the Crystallization Behavior of a Low Expansion Feldspar Glass; Journal of Dental Research (IADR Abstract No. 993) 138, 1997.

Denry IL, Mackert JR, Holloway JA, Rosenstiel SF; Effect of Cubic Leucite Stablization on the Flexural Strength of Feldspathic Dental Porcelain; Journal of Dental Research vol. 75(12): 1928–1935, Dec. 1996.

Hermansson EA, Carlsson R; On the Crystallization of the Glassy Phase in Whitewares, Transactions and Journal of the British Ceramic Society, vol. 77, 1978, pp. 32–35 XP002102546.

(List continued on next page.)

*Primary Examiner*—Melissa Koslow
*Attorney, Agent, or Firm*—Ann M. Knab

[57] ABSTRACT

A dental porcelain composition comprising a continuous glassy phase and a discontinuous, substantially uniform crystalline phase comprising cubic leucite. The porcelain exhibits coefficients of thermal expansion in the range of about 11 to about $17 \times 10^{-6}/°$ C. (measured from 25° C. to 500° C.) and fusion temperatures in the range of about 700° C. to about 1200° C. The porcelain composition of the present invention can be used to form dental restorations such as cores for all ceramic restorations. The cubic leucite phase is uniformly dispersed in the glass matrix and has an average grain size not exceeding about 4 $\mu$m and about 95% of the leucite grains do not exceed about 8 $\mu$m in diameter.

7 Claims, 4 Drawing Sheets-

OTHER PUBLICATIONS

Martin RF, Lagache M; Cell Edges and Infrared Spectra of Synthetic Leucites and Pollucites in the System $KAlSi_2O_6-RbAlSi_2O_6-CsAlSi_2O_6$; Canadian Mineralogist vol. 13, pp. 275–281 (1975).

Prasad A, Vaidyanathan TK; Crystallization of Cubic Leucite by Composition Additives+; Prepared for Presentation at the 19$^{th}$ Annual Session, American Association for Dental Research, Mar. 9, 1990.

Rouf MA, Hermansson L, Carlsson R; Crystallization of Glasses in the Primary Phase Field of Leucite in the $K2O-Al2O3-SiO2$ System; Transactions and Journal of the British Ceramic Society, vol. 77, 1978, 36–39, XP002102547.

Taylor D; Thermal Expansion Data XV. Complex Oxides with the Leucite Structure and Frameworks Based on Six–Membered Rings of Tetrahedra; Journal, vol. 90. No. 6, 197–204, 1991.

Taylor D, Henderson CMB; The Thermal Expansion of the Leucite Group of Minerals; The American Mineralogist, vol. 53, 1476–1489, Sep.–Oct., 1968.

CUBIC LEUCITE-CONTAINING DENTAL PORCELAINS

This application claims priority of Provisional Application Serial No. 60/062,345 filed on Oct. 15, 1997 which is hereby incorporated by reference.

FIELD OF THE INVENTION

This invention relates to a dental porcelain comprising cubic leucite, to a method of making a dental porcelain and to dental restorations comprising the cubic leucite porcelain.

BACKGROUND OF THE INVENTION

Leucite is a crystalline potassium aluminosilicate that, in stable form, possesses a tetragonal configuration at room temperature. Tetragonal leucite, also known as "low leucite," has been employed as a reinforcing agent in feldspathic dental porcelains. Such dental porcelain materials are described in, for example, U.S. Pat. Nos. 4,604,366 and 4,798,536. Since tetragonal leucite possesses a high coefficient of thermal expansion, the resulting feldspathic porcelains comprising tetragonal leucite dispersed therein as a discontinuous phase have correspondingly high coefficients of thermal expansion. For example, the tetragonal leucite-containing feldspathic porcelain powder sold under the trademark Optec™ by Jeneric/Pentron Inc., Wallingford, Conn. can be used to provide a dental porcelain body possessing a coefficient of thermal expansion of about $18.0 \times 10^{-6}/°$ C. when measured at 25° C. to 500° C.

When tetragonal leucite is heated to about 625° C., it changes to a cubic polymorph and exhibits a volume change of 1.2%. This transformation is reversible. Upon cooling, the cubic leucite crystals revert to the more stable tetragonal polymorph. In contrast to tetragonal leucite, the cubic form of leucite, known as "high leucite," which is otherwise unstable at room temperature, possesses a coefficient of thermal expansion of about $3 \times 10^{-6}$ (when measured at 625° to 900° C.).

The prior art discussed below shows that porcelain (also sometimes referred to as a glass-ceramic) materials containing cubic leucite stabilized at room temperature exhibit lower thermal expansion compared to tetragonal containing glass-ceramics and porcelains.

Rouf et al. in "Crystallization of Glasses in the Primary Field of Leucite in the $K_2O$—$Al_2O_3$—$SiO_2$ System" in *Trans. J. Brit. Ceram. Soc.*, 77:36–39 (1978) describe an isothermal heat treatment method of crystallizing cubic leucite in the high viscosity system of $K_2O$—$Al_2O_3$—$SiO_2$ for both powder and bulk samples which employs $TiO_2$, $ZrO_2$, and $P_2O_5$ as catalysts. The Rouf et al. method employs the use of high temperatures and long time periods and relies on the presence of large amounts of $K_2O$ (approximately 18 weight percent) in the starting glass composition to form cubic leucite as the only crystalline phase. Bulk samples of the porcelain produced by the method disclosed in Rouf et al. do not comprise cubic leucite substantially uniformly dispersed therein.

Hermansson et al. in "On the Crystallization of the Glassy Phase in Whitewares," *Trans. J. Brit. Ceram. Soc.*, 77:32–35 (1978) similarly disclose a heat treatment method of crystallizing cubic leucite in the high viscosity system of $K_2O$—$Al_2O_3$—$SiO_2$. Hermansson et al. disclose that high $K_2O$ content, a long firing time and a low content of CaO (approximately 1 weight percent) are required to stabilize the cubic phase of leucite at room temperature.

Prasad et al. in "Crystallization of Cubic Leucite By Composition Additives," 19th Annual Session, American Association For Dental Research, (1990), and Hahn et al. in "Importance of the Glass Ceramic System $K_2O$—$Al_2O_3$—$SiO_2$ in Dental Porcelain," Ceramic Forum Int./Ber. Dt. Keram. Ges. 57 (1980) No. 9–10, pp.208–214 each describe cubic leucite porcelains produced by volume crystallization of glasses containing about 2 mole % of $Cs_2O$. These porcelains are processed by a conventional method that involves smelting glass compositions with $Cs_2O$ as one of the components. The resulting glasses, aside form the presence of $Cs_2O$, are reasonably close in composition to high-strength feldspathic porcelains. The role of cesium is to stabilize the cubic leucite phase at ambient temperatures. The cubic leucite phase is formed during crystallization heat treatment following melting and is retained in the porcelains at room temperature. Although it is a simple and cost-effective method, it does not provide sufficient control of the distribution and morphology of the leucite phase. The resulting materials suffer at least from one or both of the following deficiencies: too refractory to be processed in a dental lab setting (i.e., the fusion temperature is $\geq 1200°$ C.; and grain size and uniformity of the leucite phase dispersion are not adequate to produce sufficiently strong porcelain.

None of the aforementioned prior art methods disclose a surface crystallization process. It is well known in the art that it is extremely important that the thermal expansion coefficient of a dental porcelain closely match the thermal expansion coefficient of the metal or porcelain material with which it is in contact. Since the leucite-containing dental porcelains of the prior art generally possess high coefficients of thermal expansion, they cannot be employed in combination with materials possessing significantly lower thermal expansion coefficients.

Accordingly, there is a need to for a core porcelain having a thermal expansion compatible with a variety of materials in the fabrication of dental restorations. It is desirous that an easy and cost-effective method is used to produce porcelain for such use.

SUMMARY OF THE INVENTION

These and further objects of the invention are obtained by the method of making a dental porcelain composition comprising a continuous glassy phase and a discontinuous, substantially uniform crystalline phase comprising cubic leucite. The porcelain exhibits coefficients of thermal expansion in the range of about 11 to about $17 \times 10^{-6}/°$ C. (measured from 25° C. to 500° C.) and fusion temperatures in the range of about 700° C. to about 1200° C. The porcelain composition of the present invention can be used to form dental restorations such as cores for all ceramic restorations.

The cubic leucite phase is uniformly dispersed in the glass matrix and has an average grain size not exceeding about 4 $\mu$m and about 95% of the leucite grains do not exceed about 8 $\mu$m in diameter.

In one embodiment of the method of the invention, raw materials are heated to a temperature in the range of about 1400° to 1650° C. sufficient to melt the ingredients and form a homogeneous glass melt. The duration of this melting process is in the range of approximately 2 to approximately 12 hours. The resulting glass melt is then quenched. The quenching step prevents uncontrolled spontaneous crystallization from occurring therein.

Following the quenching step, the resultant glass frit is milled or ground to a fine powder to obtain the desired particle size. The frit is milled to a powder and sieved through to $-200$ mesh ($\leq 74$ microns). The powder is then subjected to heat treatment for a period of time to promote surface crystallization thereof and provide the porcelain of this invention. Crystallization heat treatment is preferably performed in one or two steps at temperatures in the range of 50°–500° C. above the glass transition temperature of the powder for a period of time ranging from 0.5 to 12 hours. After the desired amount of crystalline material has formed, the material is quenched, crushed and reduced to a fine powder by milling for a period of time and sieved to –200 mesh. After the porcelain powder has been prepared, it is then employed in making a dental restoration in the conventional manner. The powder may be used to fabricate pellets for pressable all-ceramic restorations, net-shaped or block-shaped pre-forms (blanks) for use in CAD/CAM devices, and to form porcelain fused to metal (PFM) or all-ceramic dental restorations by conventional powder condensation techniques.

BRIEF DESCRIPTION OF THE DRAWINGS

Features of the present invention are disclosed in the accompanying drawings, wherein similar reference characters denote similar elements throughout the several views, and wherein.

DETAILED DESCRIPTION OF THE INVENTION

The present invention is directed to a porcelain composition comprising a continuous glassy phase and a discontinuous, substantially uniform crystalline phase comprising cubic leucite. The porcelain exhibits coefficients of thermal expansion in the range of about 11 to about $17 \times 10^{-6}/°$ C. and fusion temperatures in the range of about 700° C. to about 1200° C. The porcelain composition of the present invention can be used to form dental restorations such as cores for all ceramic restorations.

The cubic leucite phase is uniformly dispersed in the glass matrix and has an average grain size not exceeding about 4 $\mu$m and about 95% of the leucite grains or crystallites do not exceed about 8 $\mu$m in diameter.

In one embodiment of the invention, a glass frit composition is prepared by mixing high purity raw materials to form a resulting composition comprising about 60–about 75 mole percent $SiO_2$, about 9–about 12.5 mole percent $Al_2O_3$, about 8–about 11 mole percent $K_2O$, about 2–about 8 mole percent of an alkaline flux comprising $Li_2O$, $Na_2O$ or mixtures thereof wherein $Li_2O$ is present in an amount in the range of about 1.5 to about 4 mole percent and $Na_2O$ is present in an amount in the range of about 0.5 to about 4 mole percent, about 1–about 3 mole percent $Cs_2O$, about 3 to about 15 mole percent of an acidic flux comprising $B_2O_3$, F, $P_2O_5$ or mixtures thereof wherein $B_2O_3$ is present in an amount of up to about 5 mole percent, F is present in an amount in the range of about 3 to about 8 mole percent and $P_2O_5$ is present in an amount of up to about 2 mole percent with the remaining components of the composition, if any, including, but not limited to, one or more of, ZnO in an amount up to about 1 mole percent, CaO in an amount up to about 2 mole percent, MgO in an amount up to about 3 mole percent, $CeO_2$ in an amount up to about 0.1 mole percent, and $TiO_2$ in an amount up to 2 mole percent.

The raw materials are heated to a temperature sufficient to form a homogeneous glass melt. Preferably, the temperature at which the raw materials are melted is in the range of about 1400° to 1650° C. The resulting glass melt is then quenched. The quenching step prevents uncontrolled spontaneous crystallization from occurring therein.

Following the quenching step, the resultant glass frit is milled to a fine powder to obtain the desired particle size. The particle size effects the formation of leucite. Specifically, small particle size provides a large surface area that promotes the nucleation of leucite. The frit is milled to a powder and sieved to –200 mesh ($\leq$74 microns). Preferably, the frit is milled to less than about 25 microns and most preferably to a particle size of less than about 15 microns. The powder is then subjected to heat treatment for a period of time to promote surface crystallization thereof and provide the porcelain of this invention. Crystallization heat treatment is preferably performed in one or two steps at temperatures in the range of about 50° C.–about 500° C. above the glass transition temperature of the powder for a period of time ranging from about 0.5 to about 12 hours. The glass transition temperature for the compositions set forth above is in the range of about 400° C.–about 600° C. Preferably, the glass powder is subjected to heat treatment for a period of about 2 to about 4 hours in the temperature range of about 900° C. to about 1000° C. Alternatively, crystallization of the powder can be effected by microwave heating rather than in a conventional furnace or kiln. After the desired amount of crystalline material has formed, the material is quenched, crushed and reduced to a fine powder by milling for a period of time and sieved to –200 mesh. After the porcelain powder has been prepared, it is then employed in making a dental restoration in the conventional manner. Conventional additives such as pigments, opacifiers and like may be added to provide various shades and translucency levels. The powder may be used to fabricate pellets for pressable all-ceramic restorations, net-shaped or block-shaped pre-forms (blanks) for use in CAD/CAM devices, and to form porcelain fused to metal (PFM) or all-ceramic dental restorations by conventional powder condensation techniques. Additionally, the fusion and/or pressing temperature can be reduced by admixing the appropriate leucite-free frit of lower fusion.

One of the significant advantages of the feldspathic porcelain composition herein is that the cubic leucite crystals present therein possess average diameters less than about 4 microns and preferably less than about 2 microns. Preferably, approximately 95% of the leucite grains do not exceed 8 microns. Larger diameters may impart an undesirable rough and uneven surface and may wear away natural dentition and cause discomfort/irritation inside the oral cavity. The amount of cubic leucite crystals produced ranges from about 5 to about 70 and typically from about 40 to about 60 weight percent based on the total weight of the porcelain composition. The coefficient of thermal expansion of the resulting cubic leucite-containing porcelain composition generally ranges from about 11 to about $17 \times 10^{-6}/°$ C. when measured at 25° to 500° C. and preferably ranges from about 12 to about $15 \times 10^{-6}/°$ C. By contrast, prior art feldspathic porcelain compositions comprising leucite in the tetragonal form typically possess coefficients of thermal expansion on the order of about $18.0 \times 10^{-6}/°$ C. when measured at 25° to 500° C. The fusion temperature of the porcelain compositions of the present invention ranges broadly from about 700° to about 1200° C. and typically ranges from about 900° C. to about 1150° C.

The procedure used herein promotes surface crystallization of the cubic leucite phase due to the presence of $Cs_2O$ in the glass composition and the temperature and time of the heat treatment process. The tendency of leucite to be formed by surface crystallization is commonly regarded as a negative attribute in the glass-ceramic field, but is advantageous in the present invention.

The porcelain composition can be utilized in the fabrication of a wide variety of dental restorations such as all-ceramic restorations, porcelain-fused-to-metal restorations, inlays, onlays and veneers. It is contemplated that the porcelain composition can be utilized as a ceramic core for an all-ceramic restoration. In a particularly preferred embodiment, the powdered porcelain composition can be compacted and then partially sintered at a temperature of from about 600° to about 850° C. to form porous solid pre-forms or, if desired, fully fused at a temperature of from about 900° to about 1150° C. to form fully dense pre-forms which can be subsequently injection molded to form dental restorations utilizing the hot pressing technique. This technique is initiated by creating the restoration in wax. The wax pattern is lifted from the die and invested or surrounded by a mix of "plaster-like" material that is allowed to harden. A channel or opening leads from the outer surface of the investment into the wax pattern. Wax is eliminated from the investment during a burnout procedure. The pre-form of the feldspathic dental porcelain is placed in a special hot press (for example, the Autopress® hot press available from Jeneric/Pentron, Inc., Wallingford, Conn.) and is softened and forced under pressure into the opening of the investment. The softened material fills the void created by the wax pattern. After cooling, the hardened ceramic is broken out of the investment. Where desired, one or more layers of the porcelain herein can be applied over the ceramic core and/or color can be baked onto the surface of the restoration to simulate tooth color.

The porcelain can also be employed as an inlay, onlay or veneer to replace amalgam, gold or other porcelains. The porcelain of the present invention can be prepared as an inlay, onlay or veneer by building the porcelain powder in the form of an aqueous slurry on an appropriate refractory investment die (such as Synvest™ refractory die sold by Jeneric/Pentron Inc. of Wallingford, Conn.) and then firing the porcelain to a temperature ranging from about 800° to about 1200° C. to effect proper maturation/fusion of the porcelain. If desired, those skilled in the art can use a foil technique wherein a thin (0.001) piece of platinum or other suitable foil adapted to a gypsum die is utilized to hold porcelain in its proper geometry, the foil/porcelain is removed from the gypsum die and the porcelain is fired to effect proper maturation/fusion of the porcelain. The resultant fused specimen is placed on the prepared tooth and results in a smooth surface in contact with adjacent teeth.

A component in the starting glass composition that is beneficial to the formation of leucite by powder crystallization is LiF. LiF is the most preferred precursor for lithium and flourine ions in the resulting glass composition. LiF acts as a powerful flux during melting, lowering the viscosity and fusion temperature of the resulting glass. One possible theory is that LiF is believed to facilitate the process of surface crystallization by the action of the Li and F ions on the glass viscosity and on the surface tension and wetting of the leucite phase. In particular, the $F^{2-}$ ions counteract the effect of $Al_2O_3$ that is known to inhibit surface crystallization. Furthermore, Li may alter the thermal expansion behavior of the Cs-stabilized cubic phase as disclosed in U.S. Pat. No. 5,204,077 to Mori et al which is hereby incorporated by reference. Accordingly, a more uniform rate of thermal expansion is realized with the Cs-stabilized cubic leucite porcelain of the present invention than that exhibited with Rb-stabilized leucite porcelain disclosed in "Effect of Ion-Exchange on the Crystalliztion Behavior of a Low Expansion Feldspar Glass," by Denry et al., J. Dent Res, 76 (IADR Abstracts) 1997 and pending U.S. patent application Ser. No. 08/960,684 now U.S. Pat. No. 5,994,246 to Denry which is hereby incorporated by reference.

The following examples illustrate the practice of the present invention.

EXAMPLES

The starting materials and process parameters used in Examples 1 through 5 are displayed in Table 1. Table 2 shows the molar compositions of the feldspathic porcelains produced by the glass compositions. Table 3 displays the parameters and some of the properties obtained from the testing of the porcelains.

The starting composition mixtures listed in Table 1 were ball milled for approximately 1 hour prior to melting. The mixtures were each then charged in a coarse-grained alumina crucible and melted at 1500° C. for 4 hours. The temperature was rapidly increased to 1600° C. and the crucible was removed from the furnace and the resultant glass melt was cast into water. The glass was ball-milled into a powder and sieved to −200 mesh. The glass powder was placed into a crucible and heat-treated according to the temperature cycles shown in Table 1 to effect crystallization. The porcelain ingots formed as a result of simultaneous crystallization and sintering of the glass powder during heat-treatment were pulverized into powder again and sieved to −200 mesh.

Figure 1:
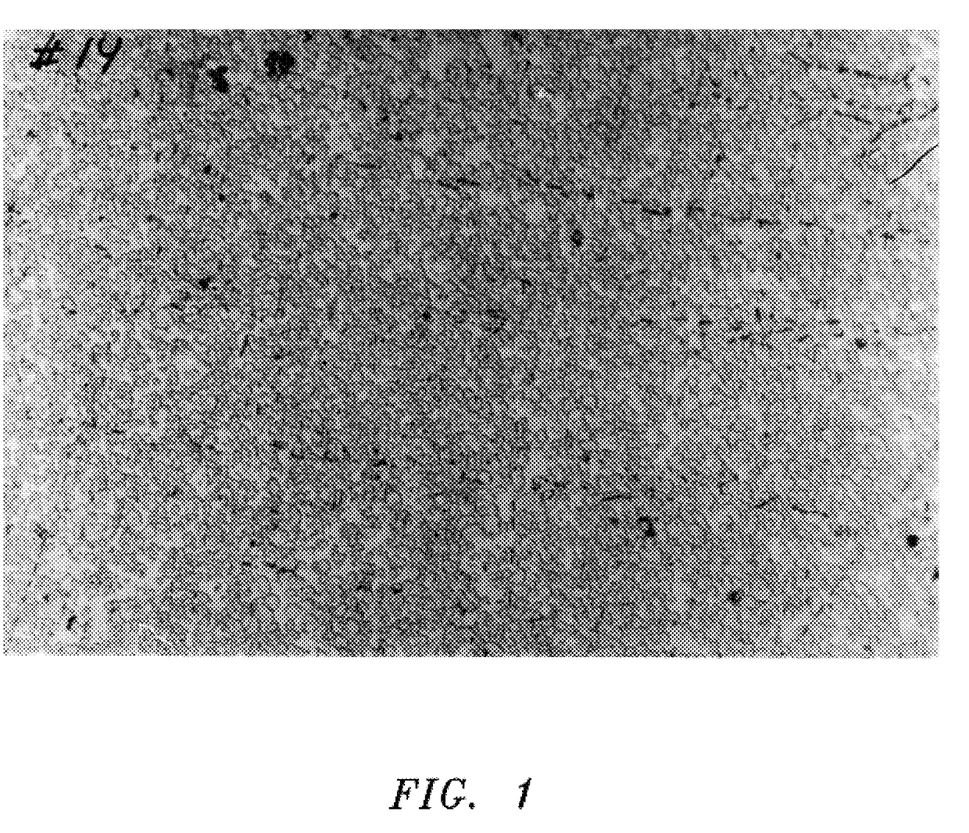
FIG. 1 is a micrograph of a polished and etched sample of the porcelain of the present invention.
Figure 2:
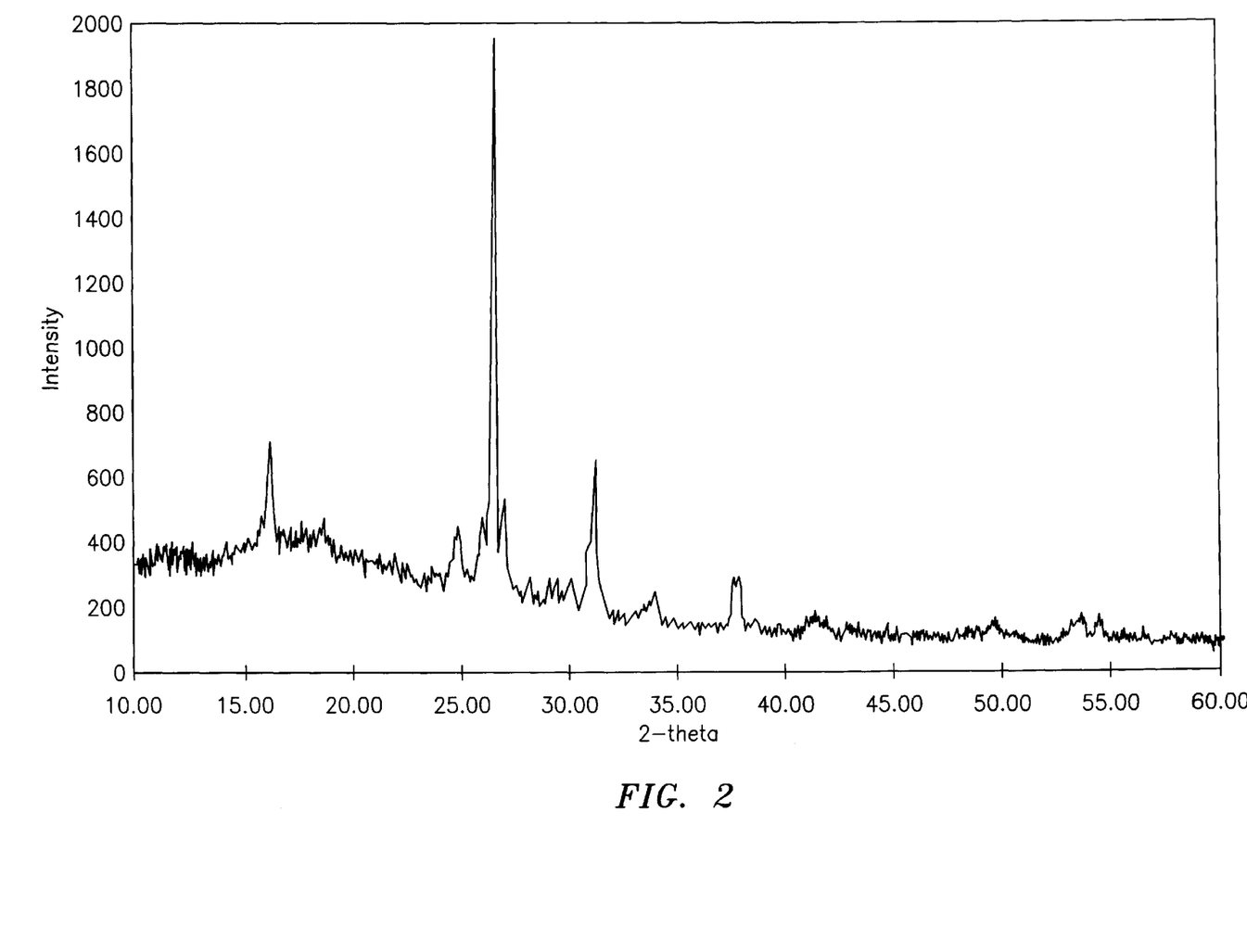
FIG. 2 is an x-ray diffraction diagram of a porcelain prepared in accordance with the present invention.
Figure 3:
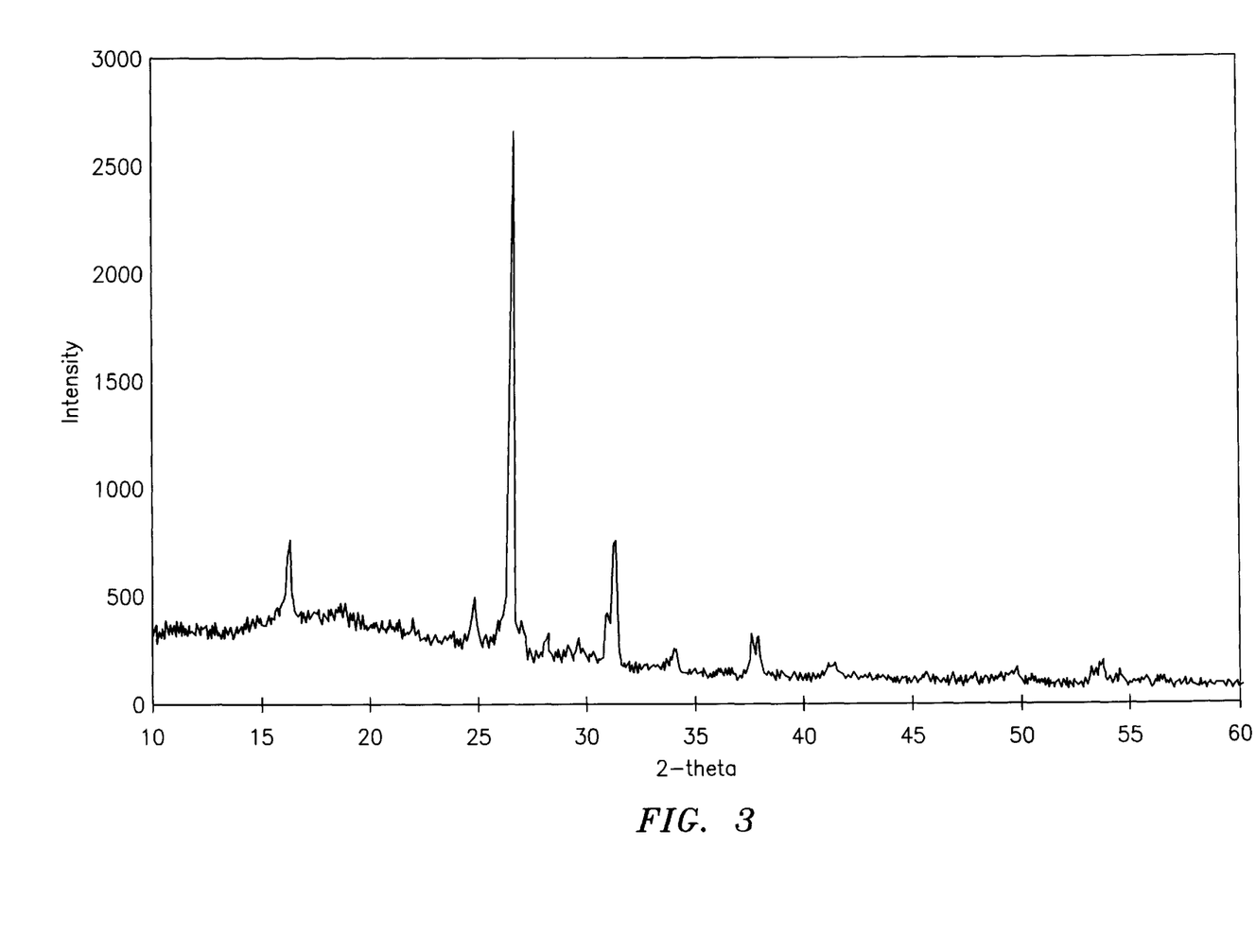
FIG. 3 is an x-ray diffraction diagram of a porcelain prepared in accordance with the present invention.
Figure 4:
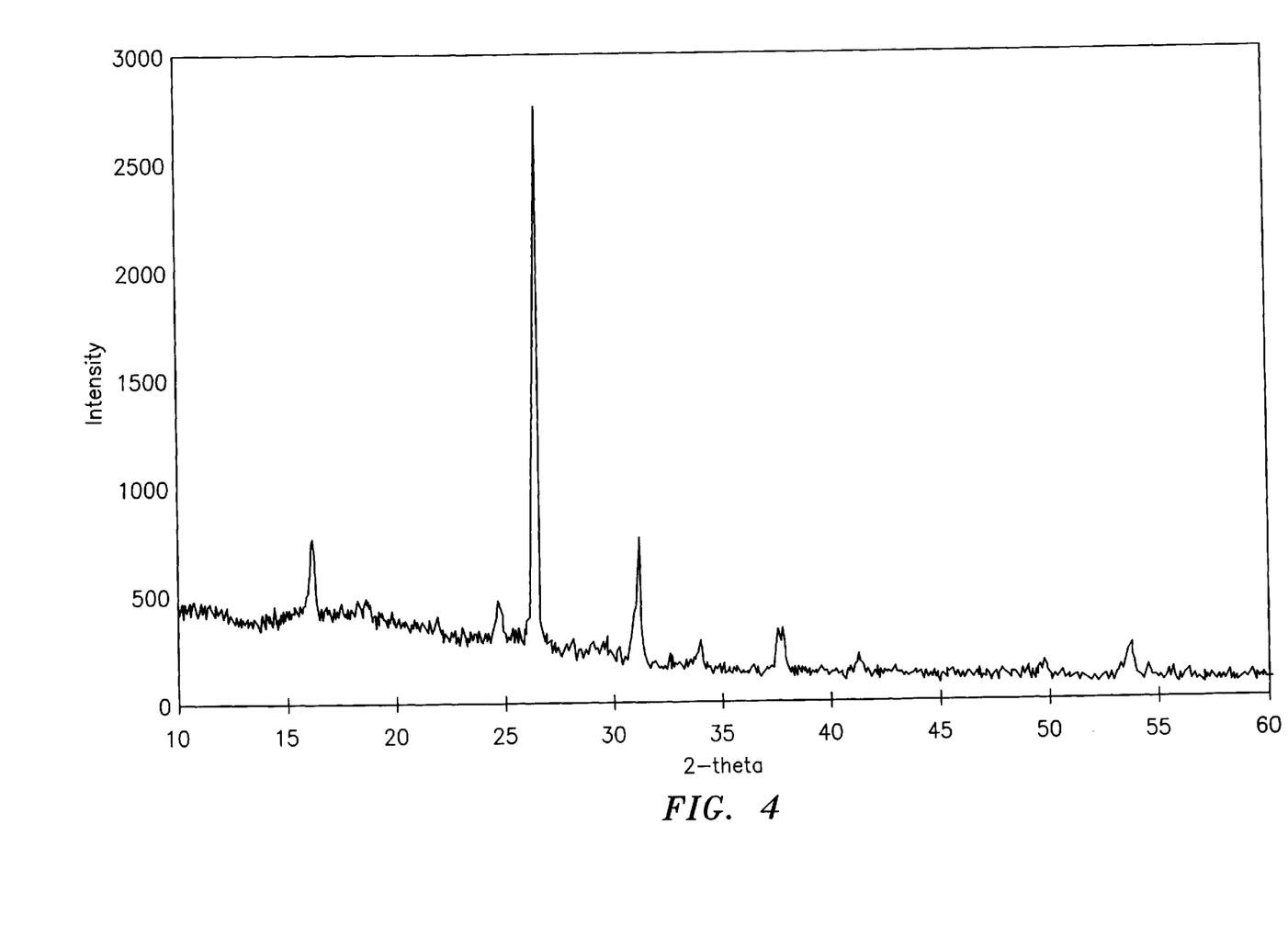
FIG. 4 is an x-ray diffraction diagram of a porcelain the present invention.

The porcelain powder was then formed into samples for microstructural analysis and thermal expansion measurements. FIG. 1 shows an optical micrograph of the porcelain described in Example 4. The micrograph shows uniform distribution of the fine-grained phase identified as cubic leucite. X-ray diffraction was performed on Examples 1, 3 and 4 and revealed the presence of cubic leucite in addition to the glassy phase. FIGS. 2 through 4 show the resulting x-ray diffraction patterns. Additionally, the porcelain powders of Examples 2 through 4 were formed into pellets. The pellets were then heat-pressed into dental restorations and rods for three-point bend tests according to well known testing techniques. Table 2 lists the compositions of the feldspathic porcelains produced from the compositions listed in Table 1. Table 3 lists the results of measurements and analyses performed. Moreover, the percent of cubic leucite is estimated to be in the range of 40–60% by volume.

TABLE 1

Starting batch compositions and properties of the produced porcelains.

| Composition (mole %) | Example 1 | Example 2 | Example 3 | Example 4 | Example 5 | Example 6 | Example 7 |
|---|---|---|---|---|---|---|---|
| $K_2CO_3$ | 16.8 | 17.1 | 17.1 | 16.9 | 17.12 | 17.1 | 17.0 |
| LiF | 2.5 | 1.8 | 1.7 | 1.7 | 1.7 | 1.7 | 1.7 |
| $Na_2CO_3$ | 5.2 | 3.9 | 3.2 | 3.1 | 3.1 | 2.5 | 2.5 |
| $Cs_2CO_3$ | 7.9 | 8.0 | 8.6 | 8.0 | 6.8 | 6.8 | 7.1 |
| $SiO_2$ | 52.7 | 54.1 | 54.3 | 53.7 | 54.4 | 54.3 | 55.1 |
| $Al_2O_3$ | 14.9 | 15.1 | 15.1 | 15.0 | 15.2 | 15.1 | 16.5 |
| $H_3BO_3$ | — | — | — | 1.6 | 1.7 | 2.5 | — |
| Heat Treatment | 900° C. × 4 hours | 900° C. × 4 hours | 900° C. × 4 hours | Loaded at 1065° C. 980° C. × 1 hr | Loaded at 1065° C. 980° C. × 1 hr | Loaded at 1065° C. 980° C. × 1 hr | Loaded at 1065° C. 980° C. × 1 hr |
| Pressing Temperature | — | 1080° C. | 1100°–1120° C. | 1100° to 1120° C. | — | — | — |

TABLE 2

Calculated molar compositions of the produced porcelains.

| Mole % | Example 1 | Example 2 | Example 3 | Example 4 | Example 5 | Example 6 | Example 7 |
|---|---|---|---|---|---|---|---|
| $SiO_2$ | 64.3 | 67.3 | 67.8 | 67.2 | 67.5 | 67.4 | 68.0 |
| $B_2O_3$ | — | — | — | 1.0 | 1.0 | 1.5 | — |
| $Al_2O_3$ | 10.7 | 11.1 | 11.2 | 11.1 | 11.1 | 11.1 | 12.0 |
| $Li_2O$ | 3.6 | 2.6 | 2.5 | 2.5 | 2.5 | 2.5 | 2.5 |
| $K_2O$ | 8.9 | 9.2 | 9.3 | 9.2 | 9.2 | 9.2 | 9.1 |
| $Cs_2O$ | 1.8 | 1.8 | 2.0 | 1.9 | 1.6 | 1.6 | 1.6 |
| $Na_2O$ | 3.6 | 2.8 | 2.2 | 2.2 | 2.2 | 1.8 | 1.8 |
| F | 7.2 | 5.2 | 5.0 | 5.0 | 5.0 | 4.9 | 5.0 |
| CaO | — | — | — | — | — | — | — |
| MgO | — | — | — | — | — | — | — |

TABLE 3

Properties of the porcelains.

| | Example 1 | Example 2 | Example 3 | Example 4 | Example 5 | Example 6 | Example 7 |
|---|---|---|---|---|---|---|---|
| Fusion Temperature | 1150° C. | 1170° C. | 1180° C. | 1170° C. | 1150° C. | 1150° C. | 1150° C. |
| CTE (25° to 500° C.) (× $10^{-6}$/° C.) | 17.2 | 15.5 | 16.1 | 14.5 | 14.1 | 14.0 | 14.5 |
| Minimum Pressing Temp ° C. | — | <1080 | <1080 | 1080 | 1080 | 1100 | 1100 |
| Glass Transition Temp. ° C. | 450 | 480 | — | 500 | 500 | 500 | 530 |
| Softening Temp. ° C. | 550 | 600 | — | 620 | 620 | 630 | >>650 |
| 3-Point Bend Strength on as pressed rods | | | | 136 ± 13 | 127 ± 17 | | |

As will be appreciated, the present invention provides porcelain compositions comprising a continuous glassy phase and a discontinuous, substantially uniform crystalline phase comprising cubic leucite useful for the fabrication of dental restorations. The porcelain exhibits coefficients of thermal expansion in the range of about 11 to about $17 \times 10^{-6}$/° C. and fusion temperatures in the range of about 700° C. to about 1200° C.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A method of making a porcelain composition which comprises heating a blend of raw materials to form a glass melt, quenching the melt to form a mass, grinding the mass to produce a powder, re-heating the powder to form a porcelain composition which comprises a continuous glassy phase and a discontinuous crystalline phase comprising cubic leucite wherein the raw materials comprise precursor materials of $SiO_2$, $Al_2O_3$, $K_2O$, LiF, $Na_2O$ and $Cs_2O$.

2. A method of making a porcelain composition which comprises heating a blend of raw materials to form a glass melt, quenching the melt to form a mass, grinding the mass to produce a powder, re-heating the powder to form a porcelain composition which comprises a continuous glassy phase and a discontinuous crystalline phase comprising cubic leucite wherein the raw materials comprise the following components in the following ranges:

$SiO_2$ about 60–about 75 mole %;
$Al_2O_3$ about 9–about 12.5 mole %;
$Li_2O$ about 1.5–about 4 mole %;
F about 3–about 8 mole %;
$K_2O$ about 8–about 9.7 mole %;
$Na_2O$ about 0.5–about 4 mole %;
$Cs_2O$ about 1–about 3 mole %;
$B_2O_3$ 0–about 5 mole %;
$P_2O_5$ 0–about 2 mole %;
wherein the mole % of $Li_2O+Na_2O$ is in the range of about 2–about 8 mole %; and
wherein the mole % of $F+B_2O_3+P_2O_5$ is in the range of about 3–about 15 mole %.

3. The method of claim 2 wherein the raw materials further comprise the following components the following ranges:

up to about 1 mole % ZnO;
up to about 2 mole % CaO;
up to about 3 mole percent MgO;
up to about 0.1 mole percent $CeO_2$; and
up to about 2 mole percent $TiO_2$.

4. A method of making a porcelain composition which comprises heating a blend of raw materials to form a glass melt, quenching the melt to form a mass, grinding the mass to produce a powder, re-heating the powder to form a porcelain composition which comprises a continuous glassy phase and a discontinuous crystalline phase comprising cubic leucite wherein the raw materials comprise the following components in the following ranges:

$SiO_2$ about 60 to about 75 mole %;
$Al_2O_3$ about 9 to about 12.5 mole %;
$K_2O$ about 8 to about 9.7 mole %;
alkaline flux about 2 to about 8 mole %;
acidic flux about 3 to about 15 mole %; and
$Cs_2O$ about 1 to about 3 mole %.

5. The method of claim 4 wherein the alkaline flux comprises alkaline flux comprises $Li_2O$, $Na_2O$ or mixtures thereof and acidic flux comprises $B_2O_3$, F, $P_2O_5$ or mixtures thereof.

6. The method of claim 5 wherein $Li_2O$ is present in an amount in the range of about 1.5 to about 4 mole percent and $Na_2O$ is present in an amount in the range of about 0.5 to about 4 mole percent.

7. The method of claim 5 wherein $B_2O_3$ is present in an amount of up to about 5 mole percent, F is present in an amount in the range of about 3 to about 8 mole percent and $P_2O_5$ is present in an amount of up to about 2 mole percent.

* * * * *